(12) United States Patent
Yamamoto et al.

(10) Patent No.: US 8,012,085 B2
(45) Date of Patent: Sep. 6, 2011

(54) METHOD FOR COLLECTING/TRANSPORTING A MEDICAL CAPSULE AND ENDOSCOPIC APPARATUS FOR THE METHOD

(75) Inventors: Hironori Yamamoto, Tochigi (JP);
Katsuaki Ohashi, Saitama (JP);
Mamoru Machiya, Saitama (JP)

(73) Assignees: SRJ Corporation, Tochigi (JP);
Fujifilm Corporation, Tokyo (JP)

( * ) Notice: Subject to any disclaimer, the term of this patent is extended or adjusted under 35 U.S.C. 154(b) by 926 days.

(21) Appl. No.: 11/478,709

(22) Filed: Jul. 3, 2006

(65) Prior Publication Data
US 2007/0015961 A1    Jan. 18, 2007

(30) Foreign Application Priority Data

Jul. 15, 2005 (JP) ................. 2005-207535
Sep. 26, 2005 (JP) ................. 2005-278438

(51) Int. Cl.
*A61B 1/04*   (2006.01)
*A61B 1/00*   (2006.01)
*A61B 1/12*   (2006.01)
(52) U.S. Cl. ......... 600/127; 600/102; 600/129; 600/156
(58) Field of Classification Search .................. 600/102, 600/115, 129, 127, 156, 128
See application file for complete search history.

(56) References Cited

U.S. PATENT DOCUMENTS

| | | | |
|---|---|---|---|
| 4,040,413 A * | 8/1977 | Ohshiro | 600/116 |
| 5,462,559 A * | 10/1995 | Ahmed | 606/140 |
| 5,653,677 A * | 8/1997 | Okada et al. | 600/112 |
| 5,685,823 A * | 11/1997 | Ito et al. | 600/127 |
| 6,524,234 B2 * | 2/2003 | Ouchi | 600/127 |
| 6,620,188 B1 * | 9/2003 | Ginsburg et al. | 607/106 |
| 6,752,755 B2 * | 6/2004 | Akiba | 600/127 |
| 6,866,627 B2 * | 3/2005 | Nozue | 600/127 |
| 7,413,543 B2 * | 8/2008 | Banik et al. | 600/129 |
| 2004/0158138 A1 | 8/2004 | Kilcoyne et al. | |

(Continued)

FOREIGN PATENT DOCUMENTS

JP    55-29338    3/1980

(Continued)

OTHER PUBLICATIONS

Hiraga, Takehito, JP2004-305505 (Machine Translation into English), Publication Date: Apr. 11, 2004, Detailed Description pp. 1-9 and Drawings pp. 1-6, and Patent Abstract of Japan page (retrieved Sep. 18, 2009 from www4.ipdl.inpit.go.jp/.*

(Continued)

*Primary Examiner* — Linda C Dvorak
*Assistant Examiner* — Alireza Nia
(74) *Attorney, Agent, or Firm* — Birch, Stewart, Kolasch & Birch, LLP

(57) ABSTRACT

The present invention provides a method for collecting/transporting a medical capsule by holding the medical capsule using an endoscopic apparatus comprising: an endoscope having an inserting section to be inserted in a body cavity with a distal end including an observation section to observe a subject and an suction opening; a sucking device in communicated with the suction opening; and a generally cylindrical hood member which is attached to the distal end of the inserting section, the method comprising: a sucking step of making an inside of the hood member vacuum by actuating the sucking device to suck the inside of the hood member through the suction opening; and a holding step of attracting and holding the medical capsule to the hood member sucked by the sucking step.

13 Claims, 14 Drawing Sheets

U.S. PATENT DOCUMENTS

| | | | |
|---|---|---|---|
| 2004/0267095 A1* | 12/2004 | Miyake et al. | 600/175 |
| 2005/0043584 A1* | 2/2005 | Nozue | 600/127 |
| 2005/0165272 A1* | 7/2005 | Okada et al. | 600/114 |

FOREIGN PATENT DOCUMENTS

| | | |
|---|---|---|
| JP | 56-143804 | 10/1980 |
| JP | 8-131397 A | 5/1995 |
| JP | 11-104063 A | 4/1999 |
| JP | 2004-194976 A | 7/2004 |
| JP | 2004-305505 A | 11/2004 |
| JP | 2004-358222 A | 12/2004 |
| WO | WO-99/32028 A2 | 7/1999 |
| WO | WO-2005/053517 A1 | 6/2005 |

OTHER PUBLICATIONS

JP Office Action issued on Mar. 8, 2011 in Japanese Application No. 2005-278436.

* cited by examiner

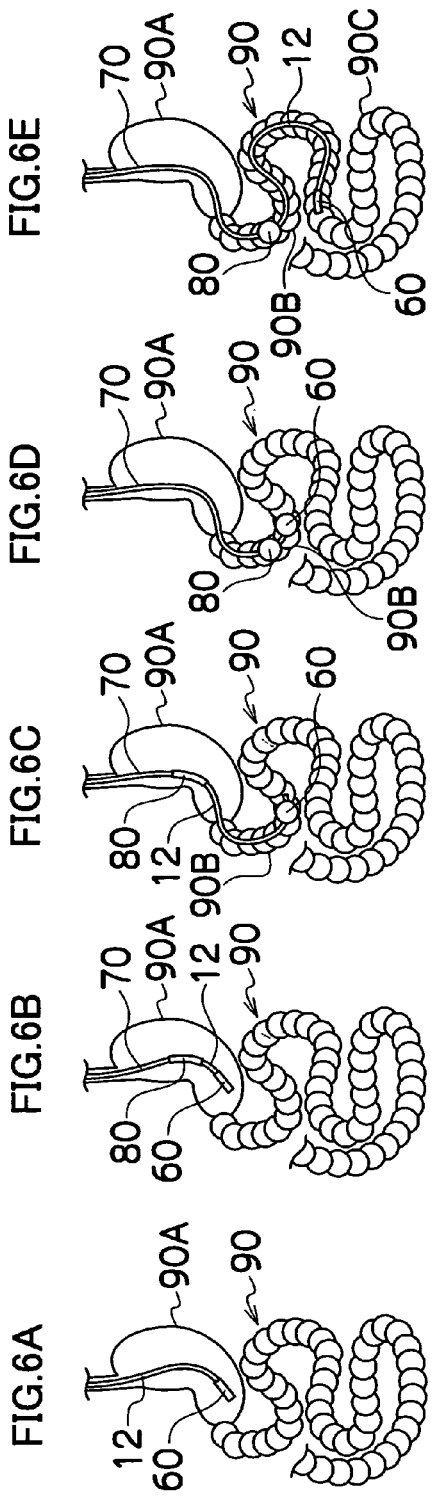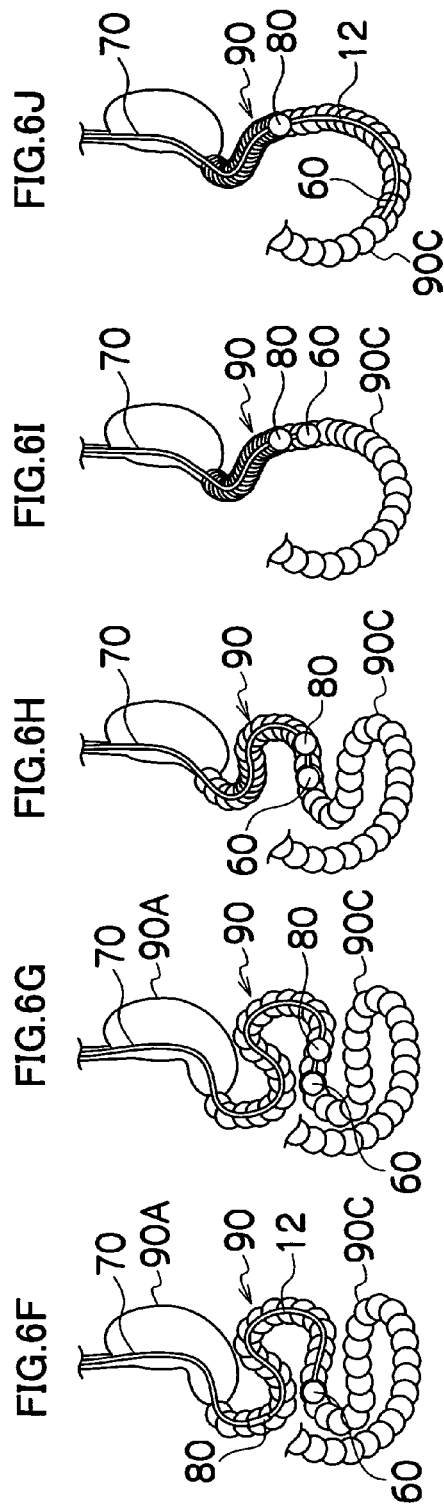

METHOD FOR COLLECTING/TRANSPORTING A MEDICAL CAPSULE AND ENDOSCOPIC APPARATUS FOR THE METHOD

BACKGROUND OF THE INVENTION

1. Field of the Invention

The present invention relates to a method for collecting/transporting a medical capsule and an endoscopic apparatus for the method, in particular, a method for holding a medical capsule in lower gastrointestinal tract such as small intestine or colon to collect or transport it and an endoscopic apparatus for the method.

2. Description of the Related Art

In recent years, as endoscopes for medical use, various types of capsule endoscopes containing miniature cameras have been developed. Because such capsule endoscopes are wireless, patient discomfort can be decreased compared to the case with an endoscope in which an inserting section of the endoscope is also inserted in his/her body cavity.

A medical capsule such as a capsule endoscope is generally expected to be naturally extruded out of a body cavity, but there is a need to collect the medical capsule at a predetermined position in a body cavity. Also, a medical capsule often gets stuck at a narrow portion of a body cavity, which requires a procedure to find the medical capsule to hold it in order to collect it or to bring it beyond the narrow portion. Moreover, in recent years, there has been a need to transport a medical capsule to a predetermined position in body cavity so that an observation can be started from the position. In these various applications, it is necessary to hold a medical capsule in a body cavity.

Then, various endoscopic apparatuses having a function to hold a medical capsule in a body cavity have been developed. For example, an endoscopic apparatus disclosed in Japanese Patent Application Laid-Open No. 2004-194976 has an inserting section with a distal end formed with a suction opening to suck and hold a medical capsule therein.

The endoscopic apparatus disclosed in Japanese Patent Application Laid-Open No. 2004-194976, however, attracts and holds a medical capsule having an outer diameter of usually on the order of 10 mm in a suction opening thereof having a small inner diameter of 2 to 4 mm, which means the endoscopic apparatus does not have a enough power to hold a capsule, and the medical capsule can be fallen.

The endoscopic apparatus disclosed in Japanese Patent Application Laid-Open No. 2004-194976 has another problem that even if a held medical capsule is fallen, the falling is not recognizable because the endoscopic apparatus holds the capsule at a position which is unlikely to be within a range for observation and it is difficult to check the capsule visually, and the fallen medical capsule has to be located again.

In addition, as the endoscopic apparatus disclosed in Japanese Patent Application Laid-Open No. 2004-194976 is generally in the form of string of scope, it cannot easily reach the inside of lower gastrointestinal tract such as small intestine to collect or transport a medical capsule.

The present invention is made in view of the above problems, and one object of the present invention is to provide a method for collecting/transporting a medical capsule which reliably holds a medical capsule in body cavity to collect or transport, and an endoscopic apparatus for the method.

SUMMARY OF THE INVENTION

To achieve the above object, a first aspect of the present invention provides a method for collecting/transporting a medical capsule by holding the medical capsule using an endoscopic apparatus comprising: an endoscope having an inserting section to be inserted in a body cavity with a distal end including an observation section to observe a subject and a suction opening; a sucking device in communicated with the suction opening; and a generally cylindrical hood member which is attached to the distal end of the inserting section, the method comprising: a sucking step of making an inside of the hood member vacuum by actuating the sucking device to suck the inside of the hood member through the suction opening; and a holding step of attracting and holding the medical capsule to the hood member sucked by the sucking step.

According to the first aspect of the present invention, the inside of a hood member is sucked through a suction opening to make the inside of the hood member vacuum so that a medical capsule can be attracted to and held by the hood member, thereby the medical capsule can be held by the hood member having a larger opening than the suction opening. Thus, a larger holding power for a medical capsule is obtained, and a medical capsule can be reliably held with it.

According to the first aspect of the present invention, as a medical capsule is held by a hood member, the held medical capsule can be observed by an observation section of an endoscope.

To achieve the above object, a second aspect of the present invention provides an endoscopic apparatus, comprising: an endoscope having an inserting section to be inserted in body cavity with a distal end including an observation section to observe a subject and an suction opening; a sucking device in communicated with the suction opening; and a generally cylindrical hood member which is attached to the distal end of the inserting section, wherein the hood member has a holding section to attract and hold a medical capsule when the sucking device is actuated to suck the inside of the hood member through the suction opening to make the inside of the hood member vacuum.

According to the second aspect of the present invention, the hood member can hold a medical capsule at the holding section thereof. Thus, a medical capsule is reliably held, which prevents the medical capsule from falling.

According to the second aspect of the present invention, as a medical capsule is held by a hood member, the held medical capsule can be observed by an observation section of an endoscope.

A third aspect of the present invention according to the second aspect provides an endoscopic apparatus, wherein the hood member is configured to hold a medical capsule with at least a part of the medical capsule being pulled into the inside of the hood member. The configuration to hold a medical capsule with at least a part of the medical capsule being pulled into the inside of the hood member increases a holding power, which can reliably prevent the medical capsule from falling.

A fourth aspect of the present invention according to the second aspect or the third aspect provides an endoscopic apparatus, wherein at least a part of the hood member is transparent or semitransparent. According to the fourth aspect of the present invention, because at least a part of the hood member is transparent or semitransparent, view is not restricted while the endoscopic apparatus is inserted to find a medical capsule, and even when the hood member holds a medical capsule, the outside of the hood member can be observed by the observation section.

A fifth aspect of the present invention according to any one of the second aspect to the fourth aspect provides an endoscopic apparatus, further comprising: a first expandable and contractible balloon which is mounted to an outer circumferential surface of the distal end of the inserting section, an insertion assisting tool into which the inserting section is inserted to be guided in a body cavity; and a second expandable and contractible balloon which is mounted to an outer circumferential surface of the insertion assisting tool.

The fifth aspect of the present invention provides a double balloon endoscopic apparatus, and this type of endoscopic apparatus makes it possible to hold a medical capsule at an inside of lower gastrointestinal tract such as small intestine.

A sixth aspect of the present invention according to any one of the second aspect to the fifth aspect provides an endoscopic apparatus, wherein the holding section is configured to include a distal end of the hood member having an inner circumferential surface which has a curved portion corresponding to a curved shape of the medical capsule.

According to the sixth aspect of the present invention, as the curved portion corresponding to a curved shape of the medical capsule is formed at an inner circumferential surface of a distal end of the hood member, the vacuum hood member has an increased airtightness so that the hood member and the medical capsule are attracted more closely to each other, which in turn increased the power to hold the medical capsule. This allows a medical capsule to be reliably held at the holding section of the hood member.

A seventh aspect of the present invention according to any one of the second aspect to the fifth aspect provides an endoscopic apparatus, wherein the holding section is configured to include a distal end of the hood member which is formed thinner than any other parts of the hood member.

According to the seventh aspect of the present invention, as the thinner distal end of the hood member is flexible, the hood member and a medical capsule are attracted closely to each other even when the hood member approaches the medical capsule at an angle. In this way, the increased airtightness of the vacuum hood member improves the power to hold the medical capsule, which allows a medical capsule to be reliably held at the holding section of the hood member.

A eighth aspect of the present invention according to any one of the second aspect to the fifth aspect provides an endoscopic apparatus, wherein he holding section is configured to include a distal end of the hood member having an inner circumferential surface in which a groove is formed in the circumferential direction.

According to the eighth aspect of the present invention, as the groove in the inner circumferential surface of the distal end of the hood member makes the distal of the hood member flexible, the closeness between the hood member and a medical capsule is not reduced even when the hood member approaches the medical capsule at an angle. In this way, the increased airtightness of the vacuum hood member improves the power to hold the medical capsule, which allows a medical capsule to be reliably held at the holding section of the hood member.

A ninth aspect of the present invention according to any one of the second aspect to the fifth aspect provides an endoscopic apparatus, wherein the holding section is configured to include a distal end of the hood member having an outer circumferential surface in which a groove is formed.

According to the ninth aspect of the present invention, as the groove in the outer circumferential surface of the distal end of the hood member makes the distal of the hood member flexible, the closeness between the hood member and a medical capsule is not reduced even when the hood member approaches the medical capsule at an angle. In this way, the increased airtightness of the vacuum hood member improves the power to hold the medical capsule, which allows a medical capsule to be reliably held at the holding section of the hood member.

A tenth aspect of the present invention according to the ninth aspect provides an endoscopic apparatus, wherein there are a plurality of the grooves in a direction along a central axis of the hood member with ribs being formed between the grooves.

According to the tenth aspect of the present invention, the grooves in a direction along the central axis of the hood member makes the distal end flexible, and the rib makes the distal end appropriately rigid.

According to the present invention, the inside of a hood member is sucked through a suction opening to make the inside of the hood member vacuum so that a medical capsule can be attracted to and held by the hood member, thereby the medical capsule can be reliably held by the hood member without falling. Also according to the present invention, as a medical capsule is held by a hood member, the held medical capsule can be observed by an observation section of an endoscope.

BRIEF DESCRIPTION OF THE DRAWINGS

FIG. 4 is a cross sectional diagram to show a distal end of an inserting section of an endoscope with a hood member being mounted to;

FIG. 6A to 6J are diagrams to illustrate a method to operate an endoscopic apparatus according to the present invention;

DETAILED DESCRIPTION OF THE PREFERRED EMBODIMENTS

Now, a preferred embodiment of a method for collecting/transporting a medical capsule and an endoscopic apparatus for the method according to the present invention will be described in detail with reference to the accompanying drawings.

Figure 1:
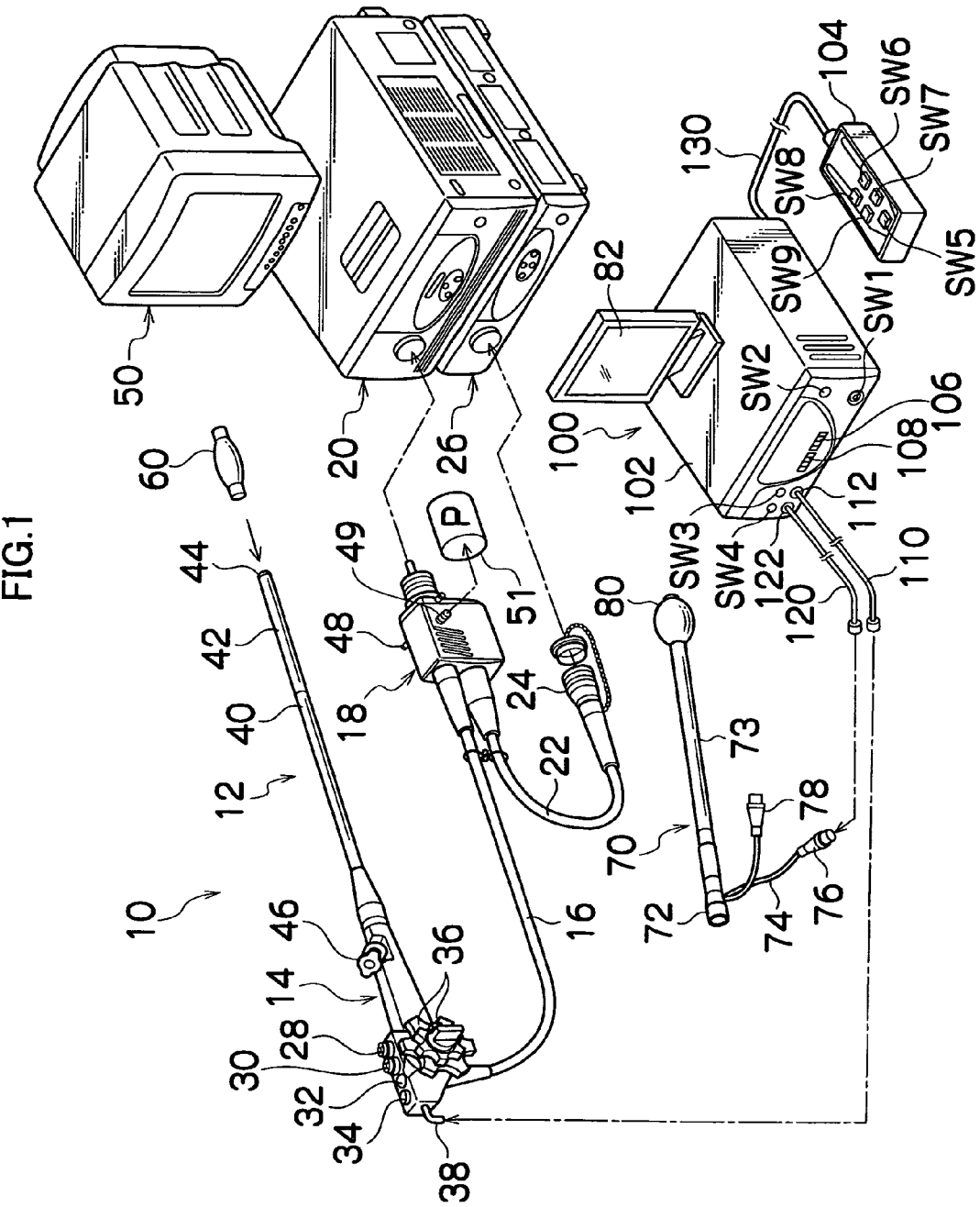
FIG. 1 is a system configuration diagram of an endoscopic apparatus according to the present invention.

FIG. 1 is a system configuration diagram to show an embodiment of an endoscopic apparatus according to the present invention. As shown in FIG. 1, an endoscopic apparatus generally comprises an endoscope 10, an insertion assisting tool 70, and a balloon controlling device 100.

The endoscope 10 comprises a hand-held control section 14 and an inserting section 12 connected to the hand-held control section 14 to be inserted into a body cavity. The hand-held control section 14 is connected to a universal cable 16 having an end which is provided with a LG connector 18. The LG connector 18 is removably coupled to a light source device 20 which sends an illumination light to an illumination optical system 54 which will be explained below (see FIG. 2). The LG connector 18 is connected to an electric connector 24 via a cable 22, the electric connector 24 being removably coupled to a processor 26.

To the hand-held control section 14, an air and water supply button 28, a suction button 30, a shutter button 32, and a function switch button 34 are arranged in a line, and a pair of angle adjustment knobs 36 are also provided therewith. The hand-held control section 14 has a rear end in which an air inlet for balloon 38 is formed with a pipe which is bent into an L shape. A supply or suction of fluids such as air through the air inlet for balloon 38 makes a first balloon 60 expanded or contracted, which will be explained below.

The inserting section 12 consists of a soft portion 40, a curved portion 42, and a distal end portion 44, starting from the hand-held control section 14, and the curved portion 42 is remotely controlled by turning the angle adjustment knobs 36 at the hand-held control section 14. This control allows the distal end portion 44 to be directed to a desired direction.

Figure 2:
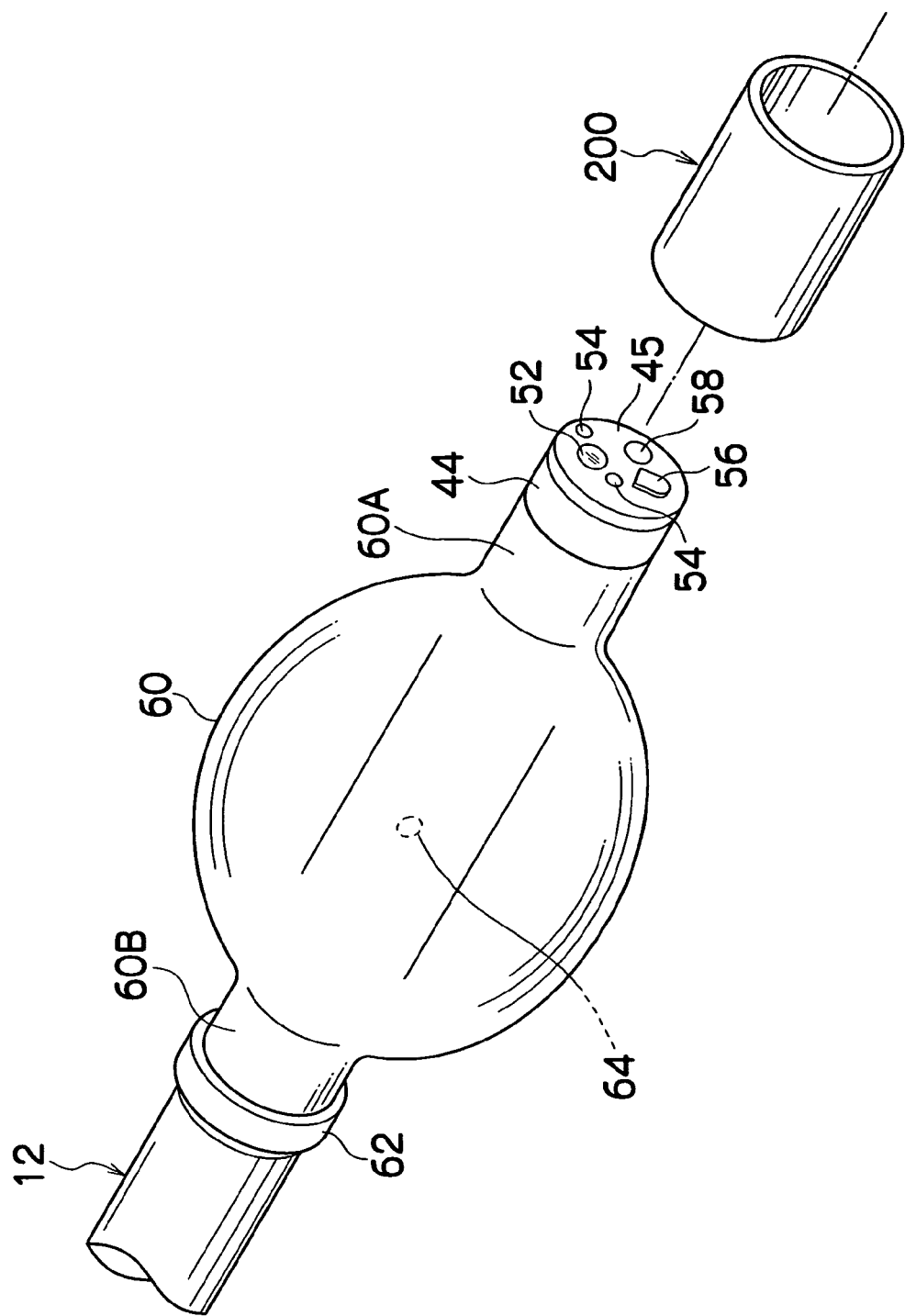
FIG. 2 is a perspective diagram to show a distal end of an inserting section of an endoscope and a hood member.

As shown in FIG. 2, the distal end portion 44 has a front surface 45 where an observation optical system 52, an illumination optical system 54, an air and water supply nozzle 56, and a forceps port (corresponds to a suction opening) 58 are provided.

Figure 3:
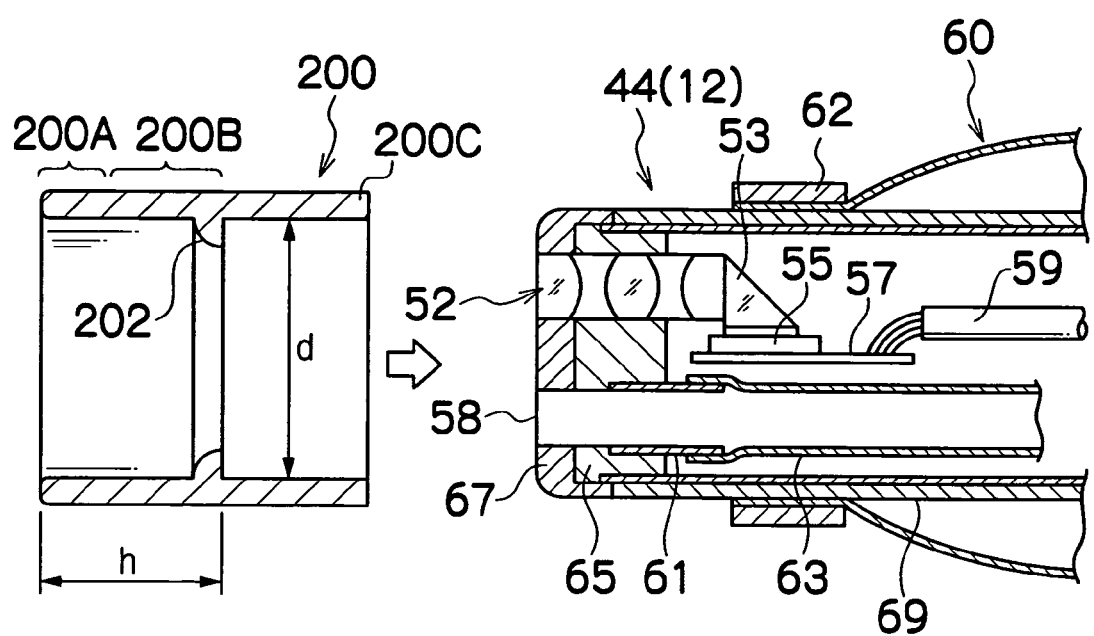
FIG. 3 is a cross sectional diagram to show a distal end of an inserting section of an endoscope and a hood member.

A prism 53 is mounted to the back of the observation optical system 52 as shown in FIG. 3, so that a light path of a light from a subject obtained through the observation optical system 52 is bent downward by the prism 53. Below the prism 53 is disposed a CCD 55 which is supported by a substrate 57, and the light from a subject which was bent by the prism 53 is focused on a light sensitive surface of the CCD 55. Then the light from a subject is converted into an electrical signal by the CCD 55 to be transmitted through a signal cable 59. The signal cable 59 is inserted through into the inserting section 12, the hand held control section 14, the universal cable 16 and the like of FIG. 1 to be extended to the electric connector 24 which is connected to the processor 26. Thus, an observation image which is obtained by the observation optical system 52 is focused on a light sensitive surface of the CCD 55 to be converted into an electrical signal, which is output through a signal cable 59 to the processor 26 where the electrical signal is converted into an image signal. In this way, a picture image from observation is displayed on a monitor 50 which is in connection with the processor 26.

Behind the illumination optical systems 54 of FIG. 2, light guides (not shown) are disposed with the outputting ends thereof. The light guides are inserted through into the inserting section 12, the hand held control section 14, the universal cable 16 and the like of FIG. 1 to dispose the inputting ends thereof in the LG connector 18. Thus, when the LG connector 18 is coupled to the light source device 20, an illumination light irradiated from the light source device 20 is transmitted through the light guides to the illumination optical systems 54 to be irradiated forward from the illumination optical systems 54.

The air and water supply nozzle 56 of FIG. 2 is in communicated with a valve (not shown) which is controlled by the air and water supply button 28 of FIG. 1, and the valve is in turn in communicated with an air and water supply connector 48 which is provided in the LG connector 18. The air and water supply connector 48 is connected with an air and water supply device (not shown) to supply air or water. Thus, an actuation of the air and water supply button 28 causes air or water to be ejected from the air and water supply nozzle 56 toward the observation optical system 52.

The forceps port 58 of FIG. 2 is in communicated with a pipe 61 which is supported by a distal end portion body 65 of FIG. 3, and the pipe 61 is in turn coupled with a tube 63. The tube 63 is inserted through into the inserting section 12 of FIG. 1 to be in communicated with a forceps inserting section 46. When a procedure tool such as a forceps is inserted into from the forceps inserting section 46, the procedure tool can be pulled out from the forceps port 58. The tube 63 of FIG. 3 is diverged along its way to be in communicated with a valve (not shown) which is controlled by the suction button 30 of FIG. 1, and the valve is in turn connected with a suction connector 49 of the LG connector 18. The suction connector 49 is connected with a suction pump (corresponds to a suction device) 51. Thus, an actuation of the suction pump 51 and an operation of the valve by the suction button 30 causes body fluid, air, and the like to be sucked through the forceps port 58.

Reference numeral 67 in FIG. 3 designates a cap mounted on the distal end surface of the distal end portion body 65, and reference numeral 69 designates a covering member which covers an outer circumferential surface of the inserting section 12.

As shown in FIG. 2, to the outer circumferential surface of the inserting section 12, a first balloon 60 is attached which is made of a resilient material such as rubber. The first balloon 60 is formed into a generally tubular shape having two deflated ends, and after the inserting section 12 is inserted through into the first balloon 60 and the first balloon 60 is disposed at a desired position, fixing rubber rings 62 are fit onto the both ends of the first balloon 60 so that the first balloon 60 is fixed around the inserting section 12.

An air vent 64 is formed in the outer circumferential surface of the inserting section 12 where the first balloon 60 is attached. The air vent 64 is in communicated with the air inlet for balloon 38 which is provided in the hand held control section 14 of FIG. 1. The air inlet for balloon 38 is connected to the balloon controlling device 100 via a tube 110. Thus, a supply or sucking air by the balloon controlling device 100 allows the first balloon 60 to be expanded or contracted. The first balloon 60 is expanded into a generally spherical shape by air supply, and is contracted to stick around the outer circumferential surface of the inserting section 12 by air suction.

Meanwhile, the insertion assisting tool 70 shown in FIG. 1 comprises a tubular and rigid holding section 72 which is provided at the rear end of the insertion assisting tool 70 and a tube body 73 which is attached to the distal end of the holding section 72, and the inserting section 12 of the endoscope 10 above described is inserted from the holding section 72 into the tube body 73.

The tube body 73 comprises a flexible resin tube substrate which is formed of urethane for example, and the substrate has an outer circumferential surface and an inner circumferential surface which are coated by a hydrophilic coating material (a lubricant coating material). The hydrophilic coating material may be, for example, polyvinyl pyrrolidone.

A second balloon 80 is attached near the distal end of the tube body 73. The second balloon 80 is formed into a tubular shape having two deflated ends, and is attached to the tube body 73 with the insertion assisting tool 70 being therethrough, and is fixed there by winding a thread (not shown) around the ends. The second balloon 80 is in communicated with a tube 74 which is adhered to the outer circumferential surface of the insertion assisting tool 70, and the tube 74 has a rear end to which a connector 76 is provided. The connector 76 is connected to a tube 120, and to the balloon controlling device 100 via the tube 120. Thus, a supply or sucking air by the balloon controlling device 100 allows the second balloon 80 to be expanded or contracted. The second balloon 80 is expanded into a generally spherical shape by air supply, and is contracted to stick around the outer circumferential surface of the insertion assisting tool 70 by air suction.

The insertion assisting tool 70 has a rear end in which an inlet 78 is formed. The inlet 78 is in communicated with an opening (not shown) which is formed in the inner circumferential surface of the insertion assisting tool 70. Thus, a lubricant (e.g. water) can be supplied into the insertion assisting tool 70 by injecting the lubricant with a syringe or the like from the inlet 78. This reduces the friction between the inner circumferential surface of the insertion assisting tool 70 and the outer circumferential surface of the inserting section 12 in inserting of the inserting section 12 into the insertion assisting tool 70, and enables a smooth relative movement between the inserting section 12 and the insertion assisting tool 70.

The balloon controlling device 100 supplies and sucks in fluids such as air through the first balloon 60, and also supplies and sucks in fluids such as air to and from the second balloon 80. The balloon controlling device 100 generally comprises a device body 102 and a hand held switch 104 for remotely controlling.

The device body 102 has a front side where a power switch SW1, a stop switch SW2, a first pressure indicator 106, a second pressure indicator 108, a first function stop switch SW3, and a second function stop switch SW4 are provided. Each of the first pressure indicator 106 and the second pressure indicator 108 is a panel to indicate a pressure value of the first balloon 60 and the second balloon 80 respectively, and the pressure indicators 106 and 108 indicate an error code in the event of failure such as a balloon burst.

The first function stop switch SW3 and the second function stop switch SW4 turn on and off the functions of the control system for endoscope A and the control system for insertion assisting tool B which will be described below, respectively, and when only one of the first balloon 60 and the second balloon 80 is used, one of the function stop switches SW3 and SW4, not in use, is controlled to be turned off. In the turned off control system A or B, any supply and suction of air is completely stopped, and the pressure indicator 106 or 108 for the system is also turned off. The initial conditions of the systems may be set by turning off both of the function stop switches SW3 and SW4. For example, a calibration for an atmosphere pressure is performed by holding down all of the switches SW5 to SW9 simultaneously on the hand held switch 104 while both of the function stop switches SW3 and SW4 are turned off.

To the front of the device body 102 are connected an air supply and suction tube 110 and an air supply and suction tube 120, for the first balloon 60 and the second balloon 80 respectively. Backflow prevention units 112 and 122 are provided at the points where each of the tubes 110 and 120 is connected to the device body 102, which prevent any backflow of body fluid when the first balloon 60 or the second balloon 80 is burst. The backflow prevention units 112 and 122 are respectively structured by fitting a filter for gas and liquid separation into the inside a hollow disk-like case (not shown) which is removably attached to the device body 102, so that the filter prevents any liquid flowing into the device body 102.

The pressure indicators 106 and 108, the function stop switches SW3 and SW4, and the backflow prevention units 112 and 122 are fixedly arranged for the endoscope 10 and for the insertion assisting tool 70. That is, the pressure indicator 106, the function stop switch SW3, and the backflow prevention unit 112 are arranged for the endoscope 10 on the right side relative to the pressure indicator 108, the function stop switch SW4, and the backflow prevention units 122 for the insertion assisting tool 70, respectively.

Meanwhile, to the hand held switch 104, a stop switch SW5 which is similar to the stop switch SW2 on the device body 102, an ON/OFF switch SW6 to give a command to pressurize/depressurize the first balloon 60, a pose switch SW7 to maintain a pressure of the first balloon 60, an ON/OFF switch SW8 to give a command to pressurize/depressurize the second balloon 80, and a pose switch SW9 to maintain a pressure of the second balloon 80 are provided, and the hand held switch 104 is electrically connected to the device body 102 via a code 130. Also, display sections to display a condition of air supply or exhaust of the first balloon 60 and second balloon 80, which are not shown in FIG. 1, are provided to the hand held switch 104.

The balloon controlling device 100 configured as described above expands each balloon 60 and 80 by supplying air, and maintains the expanded balloons 60 and 80 by controlling the air pressure in the balloons at a constant value. The balloon controlling device 100 also contracts each balloon 60 and 80 by sucking air, and maintains the contracted balloons 60 and 80 by controlling the air pressure in the balloons at a constant value.

The balloon controlling device 100 is connected to a balloon exclusive monitor 82 which displays a pressure value and an expanded or contracted condition of each balloon 60 and 80. A pressure value and an expanded or contracted condition of each balloon 60 and 80 may be displayed on the monitor 50 by superimposing on an observation image obtained by the endoscope 10.

As shown in FIG. 2, a hood member 200 is applied to the distal end portion 44 of the inserting section 12 of the endoscope 10. The hood member 200 is formed of a resin or rubber into a cylindrical shape. As shown in FIG. 3, the hood member 200 has an inner diameter d which is generally the same with or slightly smaller than the outer diameter of the distal end portion 44, thereby the hood member 200 is applied to the distal end portion 44 by elastically deforming a rear end of the hood member 200C to fit the hood member 200 onto the distal end portion 44.

The hood member 200 has an opening at its distal end having an area larger than the opening area of the forceps port 58 in the distal end portion 44. The shape of the hood member 200 is not limited to a cylinder, and the hood member 200 may be formed into any shape such as a tapered shape. However, the opening at the distal end of the hood member 200 is preferably larger than the opening area of the forceps port 58.

The hood member 200 has an inner circumferential surface having a position defining project 202 is formed to define a minimum projecting length of the hood, and the position defining project 202 contacts with the front surface of the inserting section 12 when the hood member 200 is attached to the distal end portion 44. This maintains the hood member 200 in a position projected from the distal end portion 44 when the hood member 200 is attached to the distal end portion 44. The position defining project 202 defines a minimum projecting length of the hood, the length may be increased as needed by an operator.

Figure 4:
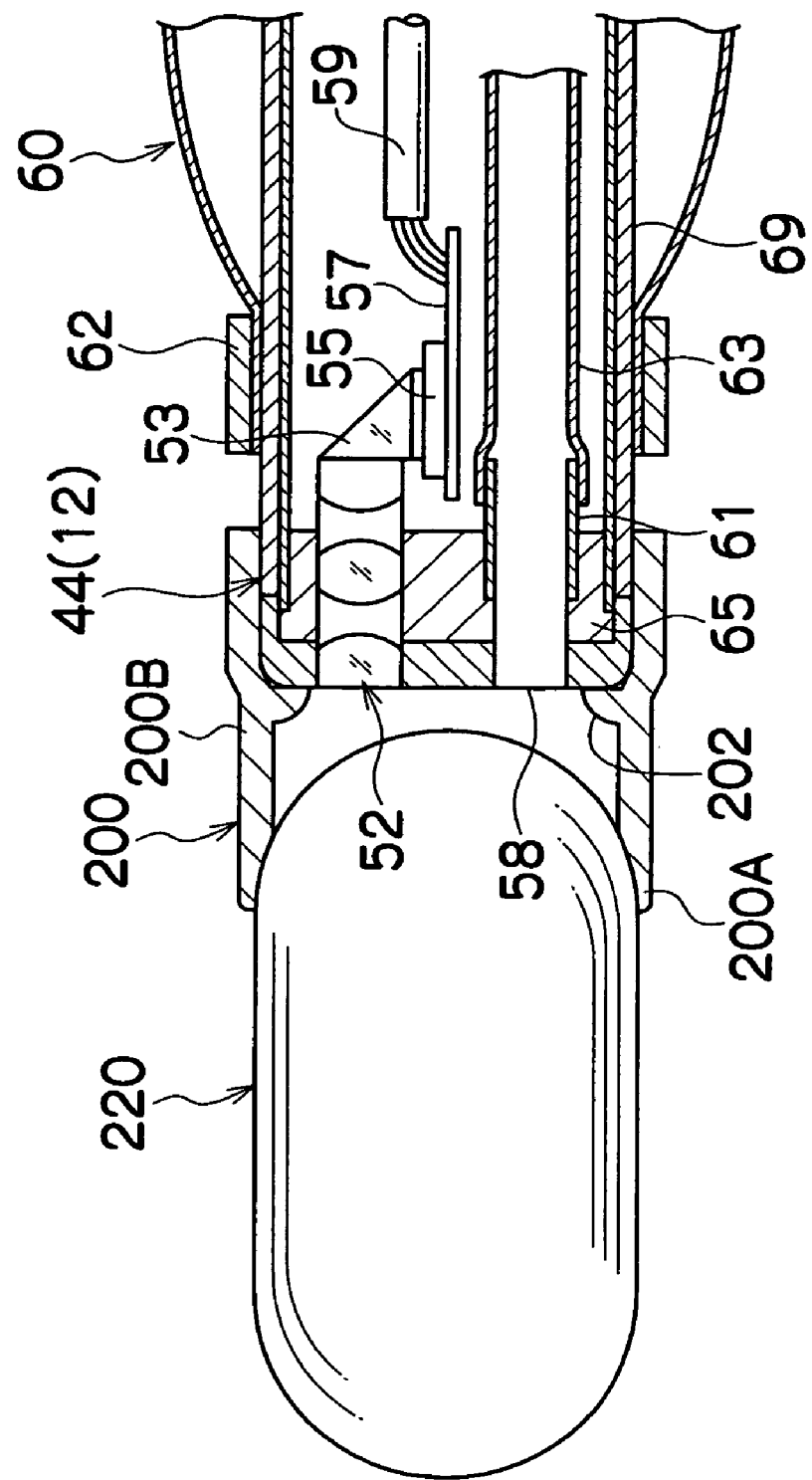
Figure 5:
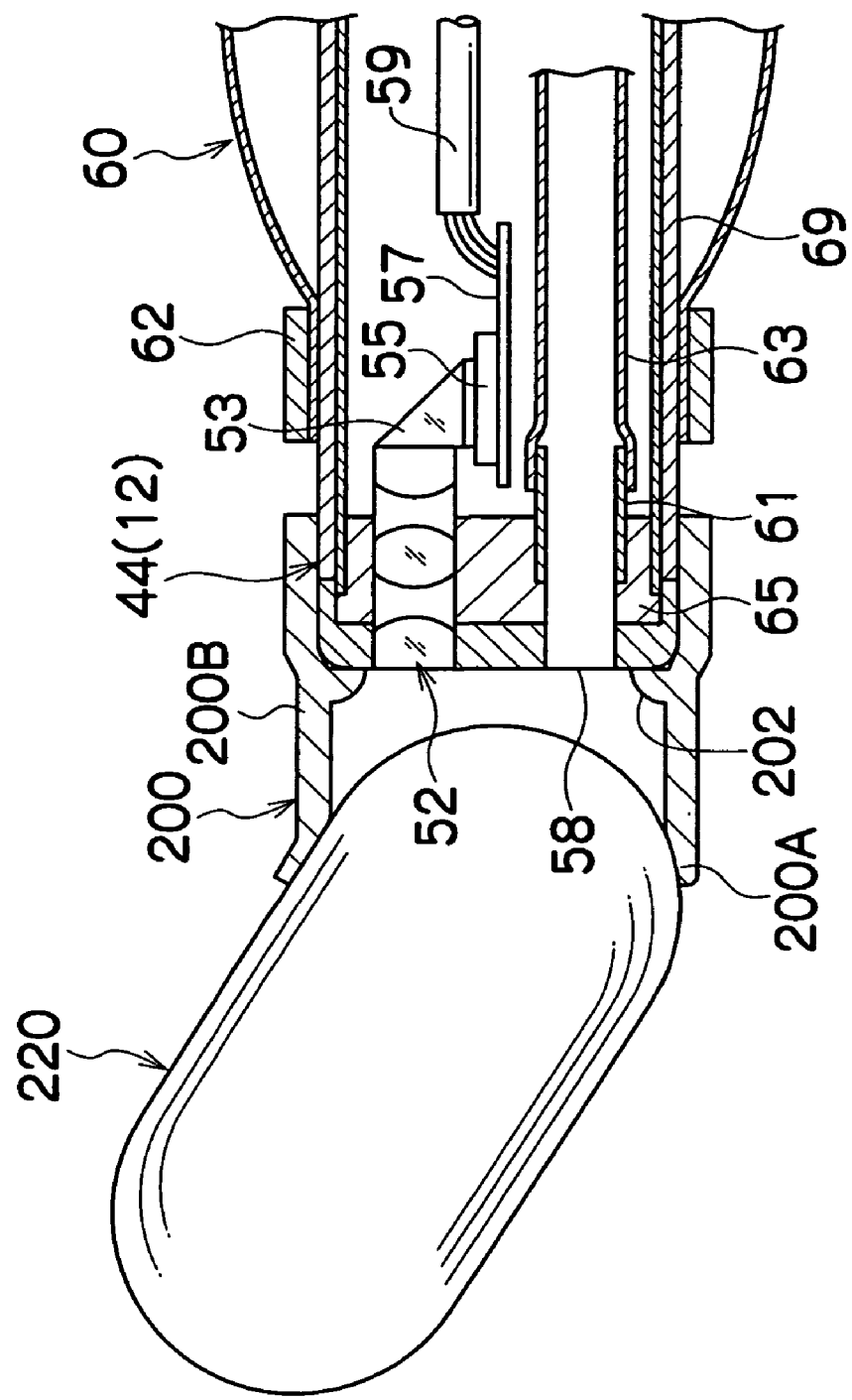
FIG. 5 is a cross sectional diagram to show a hood member which is approaching a medical capsule at an angle.

The hood member 200 has a distal end portion 200A and a middle portion 200B, and the distal end portion 200A is formed of a material which is more flexible than that for the middle portion 200B. Thus, the distal end portion 200A of the hood member 200 elastically deforms when a medical capsule 220 is attracted by the vacuum inside of the hood member 200 to the distal end portion 200A of the hood member 200, which allows the medical capsule 220 to be reliably held. That is, as shown in FIG. 4, when the medical capsule 220 is attracted to the hood member 200 with the longitudinal sides of the medical capsule 220 being generally parallel to the central axis of the hood member 200, the inner circumferential part of the distal end portion 200A of the hood member 200 elastically deforms to reliably hold the medical capsule 220. As shown in FIG. 5, when the medical capsule 220 is attracted to the hood member 200 at an angle, the distal end portion 200A of the hood member 200 elastically deforms along the medical capsule 220, which can increase an airtightness to reliably hold the medical capsule 220. In this way, the hood member 200 of this embodiment is configured to have the distal end portion 200A as a holding section to hold the medical capsule 220.

The middle portion 200B is formed of a material which is less flexible than that of the distal end portion 200A, thereby the middle portion 200B of the hood member 200 keeps its original cylindrical shape when the inside of the hood member 200 is vacuum (or in a depressurized state). This prevents any crash of the middle portion 200B of the hood member 200, which in turn prevents the medical capsule 220 from falling.

At least the middle portion 200B of the hood member 200 is formed of a transparent or semitransparent material. Thus, view is not restricted while the hood member 200 is inserted in a body cavity to find the medical capsule 220, and when the medical capsule 220 is held at the distal end portion 200A of the hood member 200, the outside of the hood member 200 can be observed through the transparent or semitransparent middle portion 200B. The entire of the hood member 200 may be formed of a transparent or semitransparent material.

Now, a method to insert the inserting section 12 of the endoscopic apparatus which is configured as described above into a body cavity will be explained with reference to FIGS. 6A to 6J. FIGS. 6A to 6J show an example to insert an endoscopic apparatus by oral route, but the endoscopic apparatus may be inserted by anal route.

First, the first balloon 60 and the second balloon 80 are contracted and the inserting section 12 is inserted into the insertion assisting tool 70 to start the insertion of the inserting section 12. As shown in FIG. 6A, when the distal end of the inserting section 12 reaches the inside of stomach 90A, the insertion assisting tool 70 is inserted along the inserting section 12, so that, as shown in FIG. 6B, the distal end of the insertion assisting tool 70 reaches the inside of the stomach 90A.

Next, while holding the insertion assisting tool 70 so as not to be pulled out of the body cavity, the inserting section 12 is inserted into the insertion assisting tool 70 until the distal end of the inserting section 12 reaches the second portion of duodenum 90B as shown in FIG. 6C (an inserting operation). Then the first balloon 60 is expanded to fix the distal end of the inserting section 12 to the second portion of duodenum (a fixing operation).

Then the insertion assisting tool 70 is pushed down to be inserted along the inserting section 12 (a pushing operation). As shown in FIG. 6D, after the distal end of the insertion assisting tool 70 comes close to the first balloon 60, the second balloon 80 is expanded by supplying air. This fixes the second balloon 80 to the second portion of duodenum 90B, which holds the second portion of duodenum 90B around the insertion assisting tool 70 via the second balloon 80 (a holding operation).

In this holding state, both of the insertion assisting tool 70 and the inserting section 12 are drawn back (a drawing back operation). This removes any excess deflection or bending between the entrance and the second portion of duodenum 90B of the gastrointestinal tract 90.

Next, after the air in the first balloon 60 is sucked to contract the first balloon 60 as shown in FIG. 6E, the inserting section 12 is inserted into the small intestine 90C (an inserting operation). Because any excess deflection or bending between the entrance and the second portion of duodenum 90B of the gastrointestinal tract 90 is already removed by the insertion assisting tool 70, the inserting section 12 can be readily inserted.

Next, as shown in FIG. 6F, the first balloon 60 is expanded to fix the distal end of the inserting section 12 to the gastrointestinal tract 90 (a fixing operation). After the second balloon 80 is contracted, as shown in FIG. 6G, the insertion assisting tool 70 is pushed down to be inserted along the inserting section 12 (a pushing operation), so that the distal end of the insertion assisting tool 70 comes close to the first balloon 60 to expand the second balloon 80 (a holding operation).

Then, as shown in FIG. 6H, while the first balloon 60 and the second balloon 80 are expanded, both of the insertion assisting tool 70 and the inserting section 12 are drawn back (a drawing back operation). This removes any excess deflection or bending of the gastrointestinal tract 90.

This series of operations described above (an inserting operation, a fixing operation, a pushing operation, a holding operation, and a drawing back operation) is repeatedly performed, and as a result, the gastrointestinal tract 90 which has been complicatedly bent or deflected is made simplified as shown in FIG. 6I. This allows the inserting section 12 to be inserted further into the gastrointestinal tract 90 as shown in FIG. 6J.

Now, operations of the endoscopic apparatus according to the present invention will be explained. An example is shown below in which a medical capsule 220 in a body cavity is held to be collected at outside of the body cavity.

First, the inserting section 12 is inserted into a body cavity with a hood member 200 being attached to the distal end portion 44 of the inserting section 12. For example, operations such as those described with FIGS. 6A to 6J are performed to insert the distal end portion 44 of the inserting section 12 into a lower gastrointestinal tract such as small intestine.

Then, the distal end portion 44 of the inserting section 12 is inserted to a position where a medical capsule 220 is located, the distal end portion 200A of the hood member 200 is brought close to the medical capsule 220 in the body cavity while observing image obtained by the observation optical system 52.

The suction button 30 is controlled to start a sucking through the forceps port 58. This causes the gas (or liquid) in the hood member 200 to be sucked through the forceps port 58, and the inside of the hood member 200 is made vacuum.

Due to the vacuum inside of the hood member 200, the medical capsule 220 is attracted to the distal end portion 200A of the hood member 200. As the distal end portion 200A of the hood member 200 is formed of a flexible material, the medical capsule 220 is reliably attracted to and held by the distal end portion 200A of the hood member 200, in spite of a posture of the medical capsule 220. Also, as the medical capsule 220 is attracted to and held by the distal opening of the hood member 200 the area of which is larger than that of the forceps port 58, the medical capsule 220 is reliably held with a larger holding power. In addition, the medical capsule 220 is held with a part of the medical capsule 220 being pulled into the inside of the hood member 200, which increases closeness due to increased airtightness between the medical capsule 220 and the hood member 200, so that the holding power for the medical capsule 220 is increased. Thus, the medical capsule 220 can be more reliably held.

After the medical capsule 220 is held, the inserting section 12 of the endoscope 10 is withdrawn out of the body cavity to bring the medical capsule 220 to the outside of the body cavity and collect it. During this operation, as the medical capsule 220 is held in a region where can be observed by the observation optical system 52, the holding of the medical capsule 220 can be continuously checked visually from an observation image. Thus, in case of the medical capsule 220 being fallen, the situation would be immediately known.

During the withdrawing of the inserting section 12 of the endoscope 10 out of the body cavity, as the middle portion 200B of the hood member 200 is transparent or semitransparent, the outside of the hood member 200 can be observed. This prevents the held medical capsule 220 from being stuck to a wall surface and the like of the body cavity.

As described above, according to the endoscopic apparatus of this embodiment, the inside of the hood member 200 is sucked through the forceps port 58 to be vacuum, so that a medical capsule 220 is attracted to and held by the distal end portion 200A of the hood member 200. Because the distal end portion 200A of the hood member 200 has an opening the area of which is larger than that of the forceps port 58, the distal end portion 200A has a larger power to hold the medical capsule 220. So, according to this embodiment, the medical capsule 220 can be reliably held and collected without falling.

According to this embodiment, because the medical capsule 220 is held by the hood member 200, the held medical capsule 220 can be continuously checked visually from an observation image obtained by the observation optical system 52.

Figure 7:
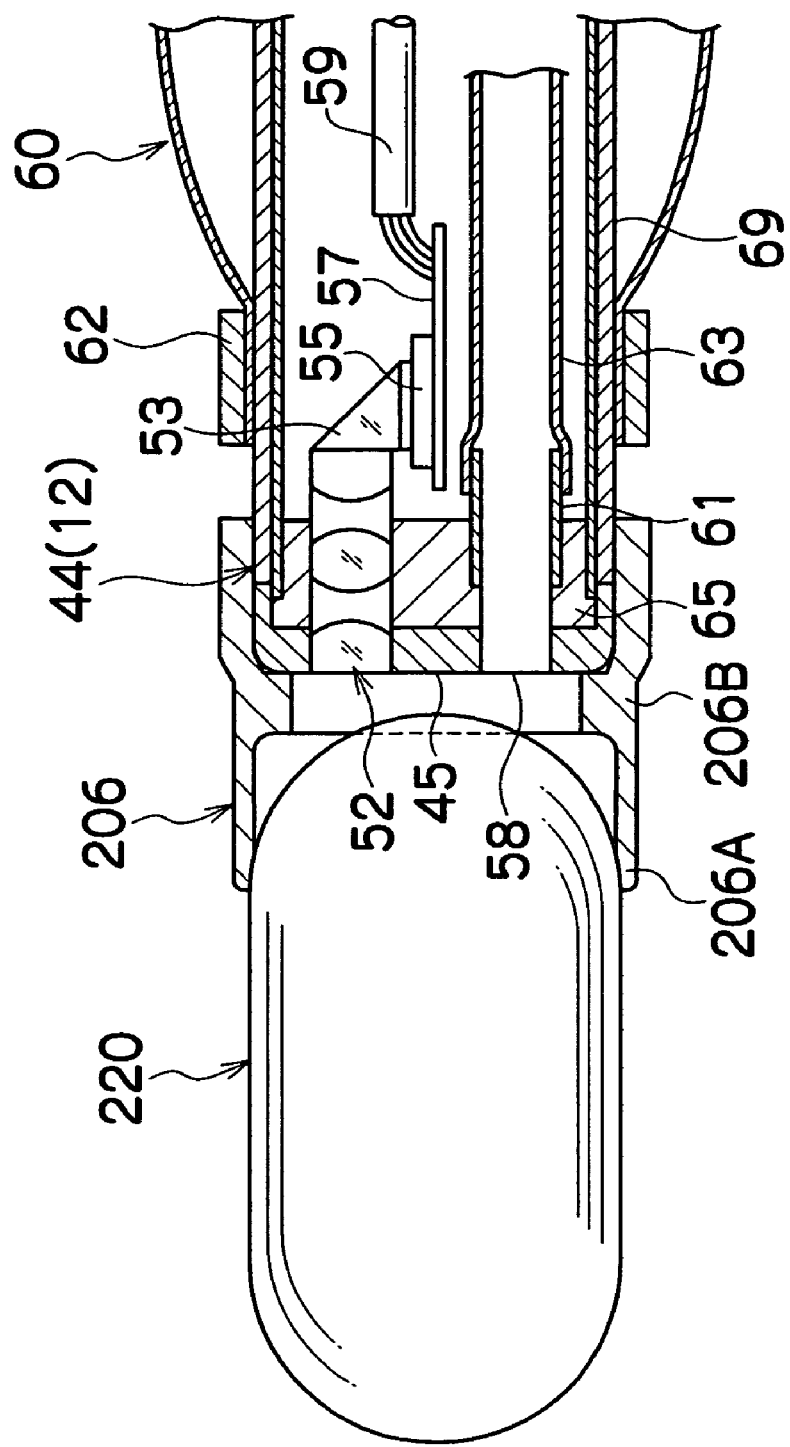
FIG. 7 is a cross sectional diagram to show a hood member having a different configuration from that of FIG. 4.
Figure 8:
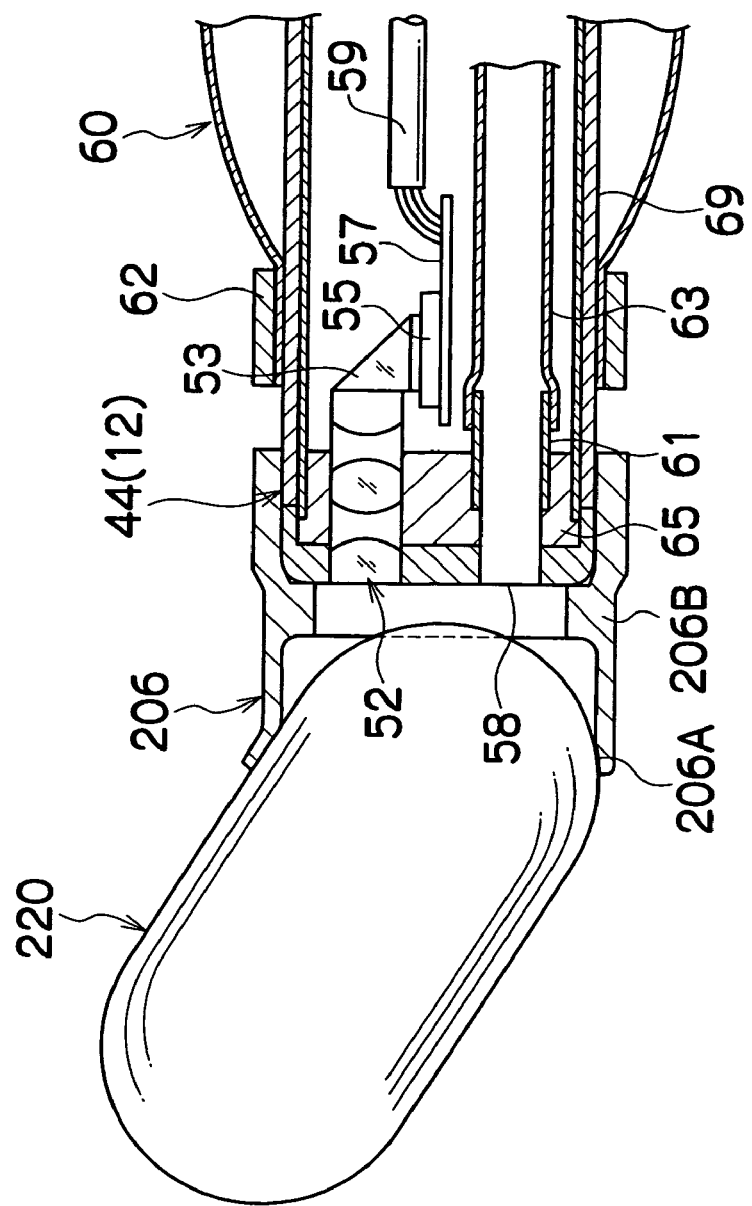
FIG. 8 is a cross sectional diagram to show the hood member of FIG. 7 which is approaching a medical capsule at an angle.

The configuration of the holding section in the hood member 200 is not limited to the above embodiment, but the holding section in the hood member 200 may be configured in any way which is appropriate to hold a medical capsule 220. For example, a hood member 206 shown in FIG. 7 includes a distal end portion 206A and a middle portion 206B, the distal end portion 206A having a thickness smaller than that of the middle portion 206B so that the distal end portion 206A is easily deflected. So, as shown in FIG. 8, even when the hood member 206 approached the medical capsule 220 at an angle, the distal end portion 206A of the hood member 206 is deflected to closely contact with the medical capsule 220. This increases closeness due to increased airtightness between the medical capsule 220 and the hood member 206, so that the holding power for the medical capsule 220 is increased. Thus, the medical capsule 220 can be reliably held. The middle portion 206B of the hood member 206 of FIG. 7 and FIG. 8 is formed thicker than the distal end portion 206A with an inner circumferential surface of the middle portion 206B being projecting inward, and the middle portion 206B also functions as a positioning element when it contacts with the front surface 45 of the inserting section 12. The thick middle portion 206B keeps its original cylindrical shape even when the inside of the hood member 206 is sucked vacuum. This prevents the attracting power from being decreased due to a crash of the middle portion 206B, which in turn prevents the medical capsule 220 from falling.

Figure 9:
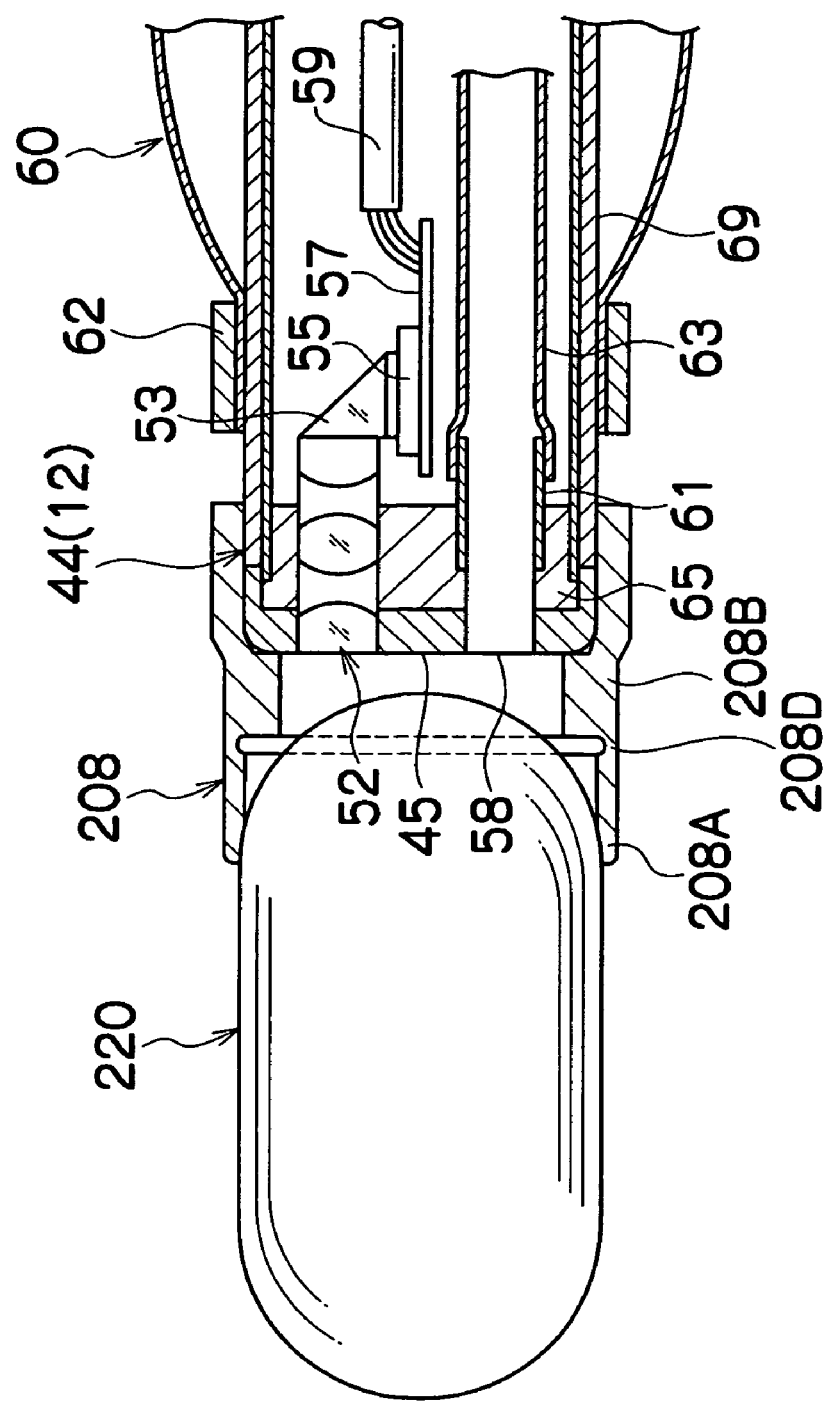
FIG. 9 is a cross sectional diagram to show a hood member having a different configuration from that of FIG. 7.
Figure 10:
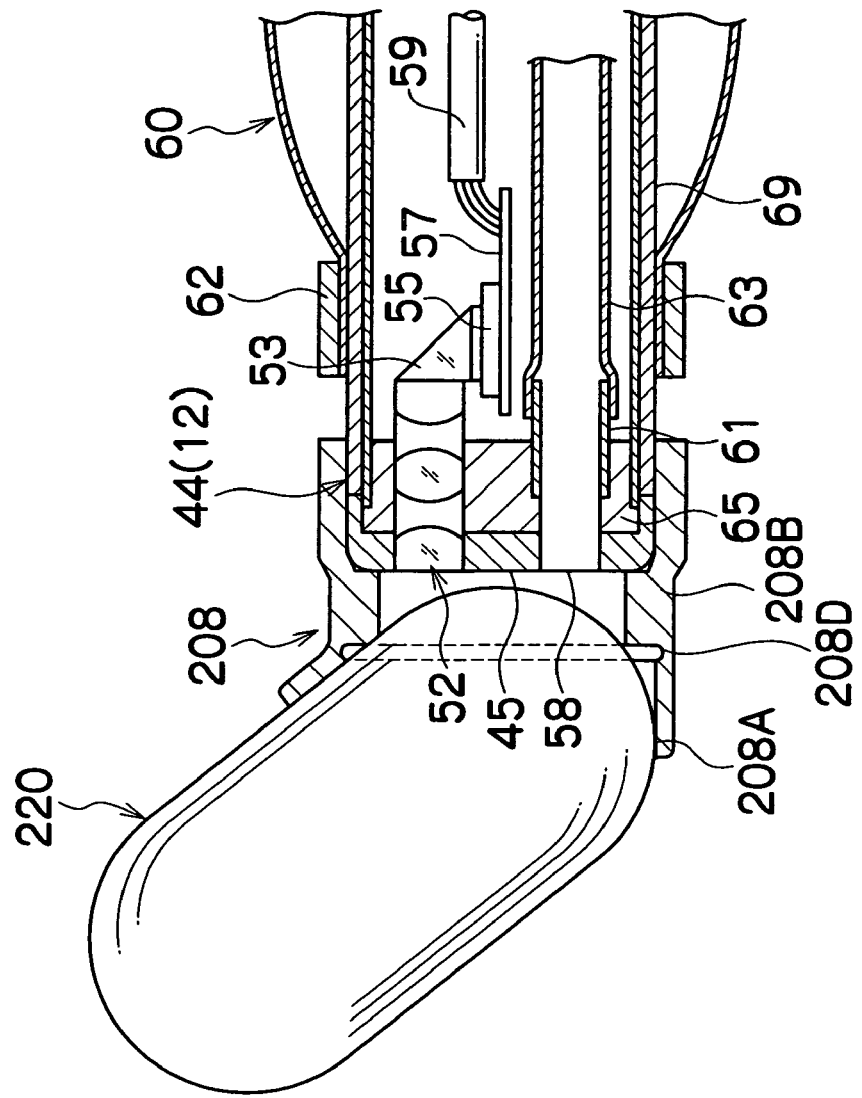
FIG. 10 is a cross sectional diagram to show the hood member of FIG. 9 which is approaching a medical capsule at an angle.

A hood member 208 shown in FIG. 9 has a distal end portion 208A and a middle portion 208B, and a groove 208D is formed between the distal end portion 208A and the middle portion 208B. The groove 208D is annularly formed in an inner circumferential surface of the hood member 208 in a circumferential direction thereof. The groove 208D of this configuration reduces the rigidity of the distal end portion 208A of the hood member 208, which allows the distal end portion 208A to be easily deflected. This increases closeness due to increased airtightness between the medical capsule 220 and the distal end portion 208A of the hood member 208, so that the holding power for the medical capsule 220 is increased. Thus, the medical capsule 220 can be reliably held. Especially, as shown in FIG. 10, even when the hood member 208 approaches the medical capsule 220 at an angle, the distal end portion 208A of the hood member 208 is deflected to closely contact with the medical capsule 220, thereby the medical capsule 220 can be reliably held.

Figure 11:
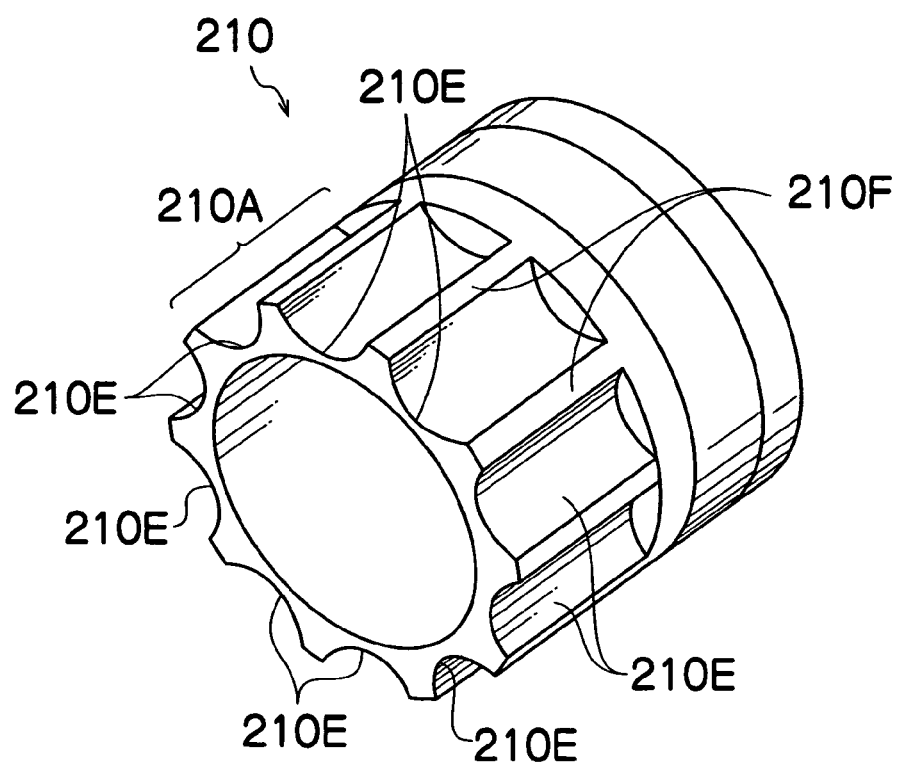
FIG. 11 is a perspective diagram to show a hood member having a different configuration from that of FIG. 2.

A hood member 210 shown in FIG. 11 includes a distal end portion 210A having an outer circumferential surface provided with a plurality of grooves 210E. Each of the grooves 210E is formed in an axis direction of the hood member 210, and has a circular cross section which is perpendicular to the axis direction. The grooves 210E are separated by a uniform distance from each other in the circumferential direction, and ribs 210F are formed between the grooves 210E. The grooves 210E allow the distal end portion 210A of the hood member 210 to be easily deflected, and the ribs 210F allow the distal end portion 210A of the hood member 210 to maintain its appropriate rigidity. In addition, the grooves 210E formed in the outer circumferential surface make the inner circumferential surface smooth which readily contacts closely with a medical capsule 220. This increases closeness between the medical capsule 220 and the hood member 210, so that the medical capsule 220 can be more reliably held.

Figure 12:
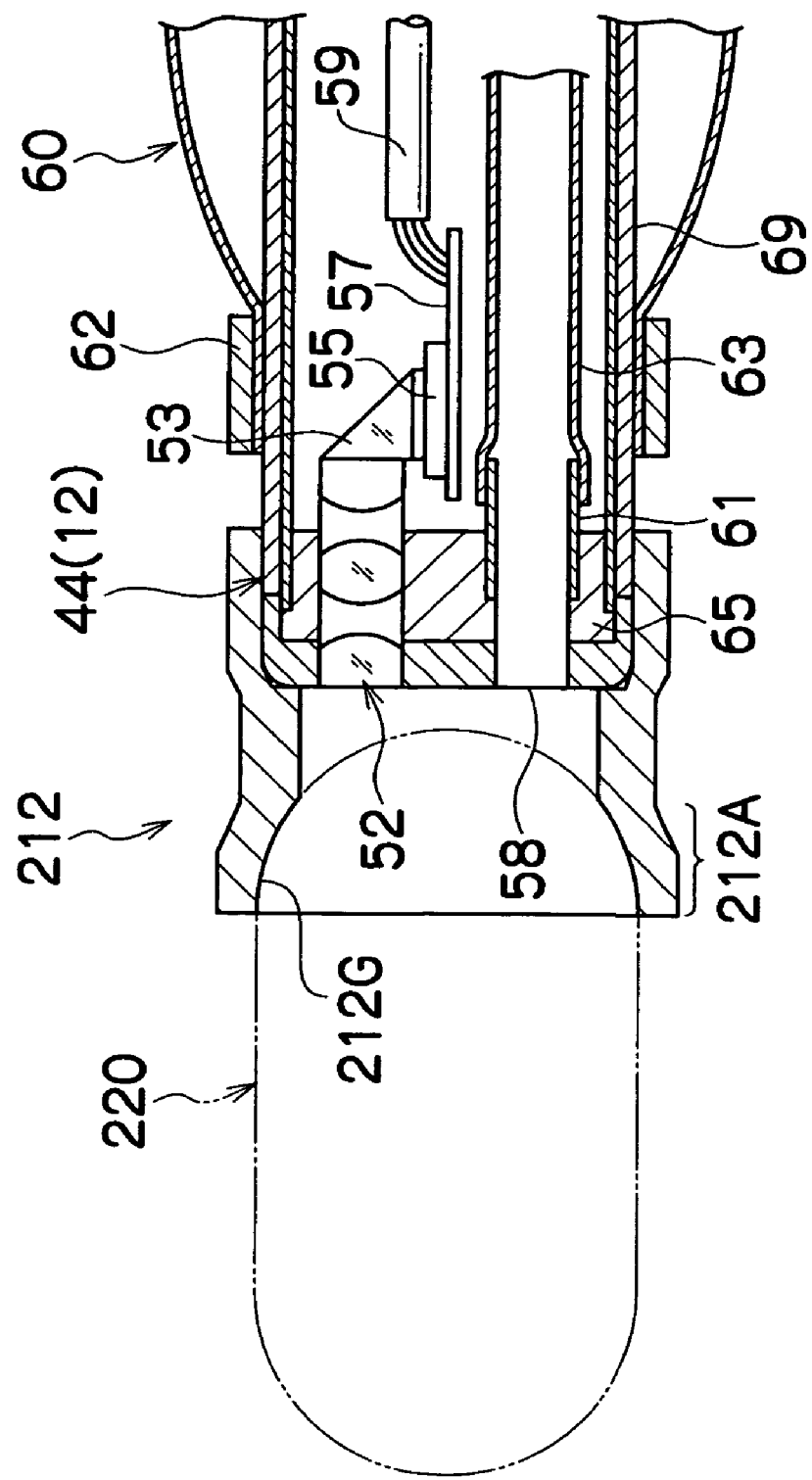
FIG. 12 is a cross sectional diagram to show a hood member having a different configuration from that of FIG. 4.

A hood member 212 shown in FIG. 12 includes a distal end portion 212A having an inner circumferential surface which is formed to correspond to the curved shape of a medical capsule 220. That is, the distal end portion 212A of the hood member 212 has on its inner circumferential surface a curved surface portion 212G which corresponds to a part of the sphere of a medical capsule 220. Thus, when a medical capsule 220 is attracted to and held by the distal end portion 212A, the closeness between the medical capsule 220 and the distal end portion 212A of the hood member 212 is increased, so that the medical capsule 220 can be more reliably held.

Figure 13:
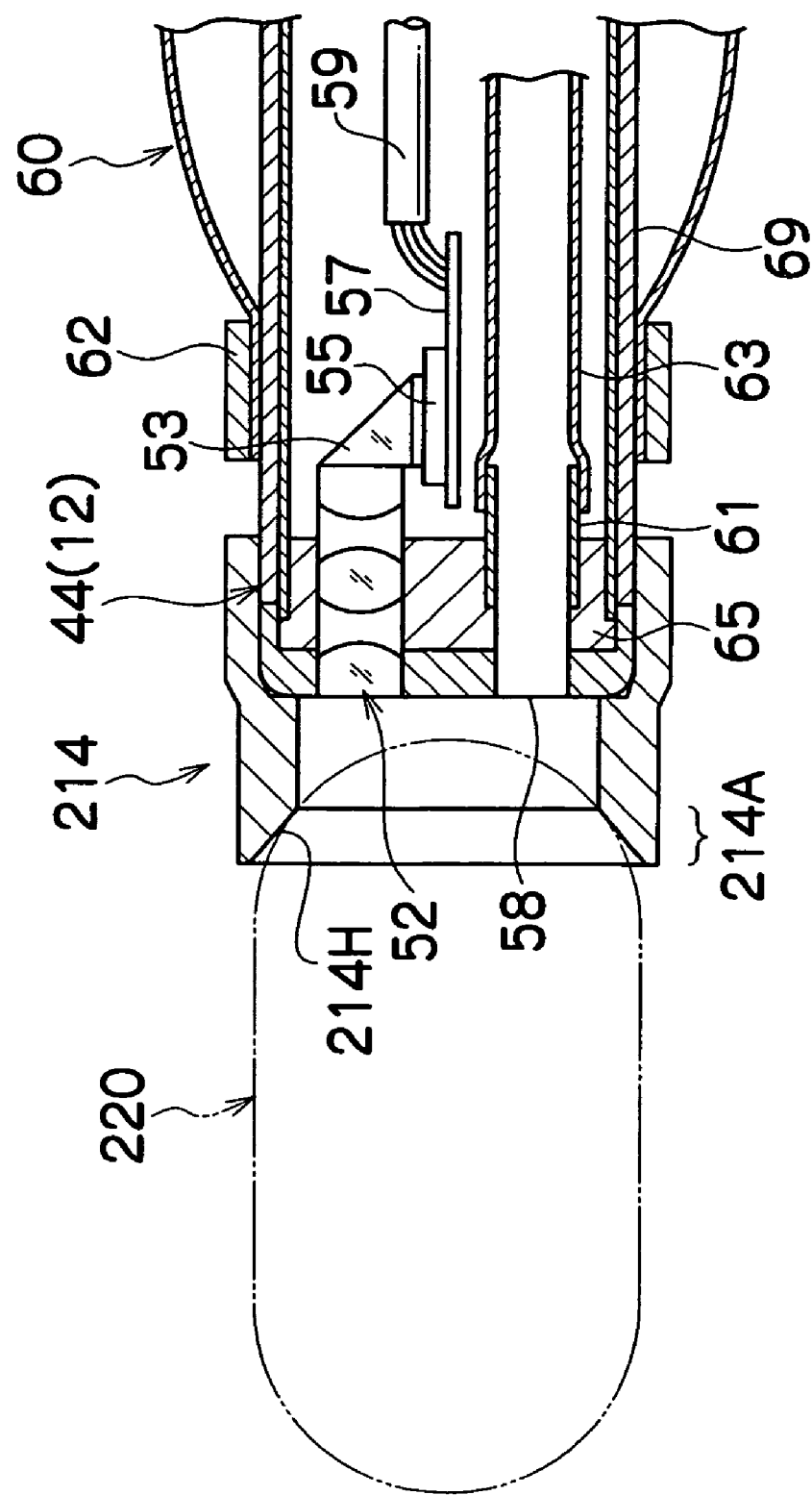
FIG. 13 is a cross sectional diagram to show a hood member having a different configuration from that of FIG. 12.

A hood member 214 shown in FIG. 13 includes a distal end portion 214A having an inner circumferential surface which has a taper 214H to provide a holding section. Thus, when a medical capsule 220 is attracted to and held by the distal end portion 214A, the taper 214H contacts with the curved portion of the medical capsule 220, which increases closeness between the hood member 214 and the medical capsule 220, so that the medical capsule 220 can be more reliably held.

Figure 14:
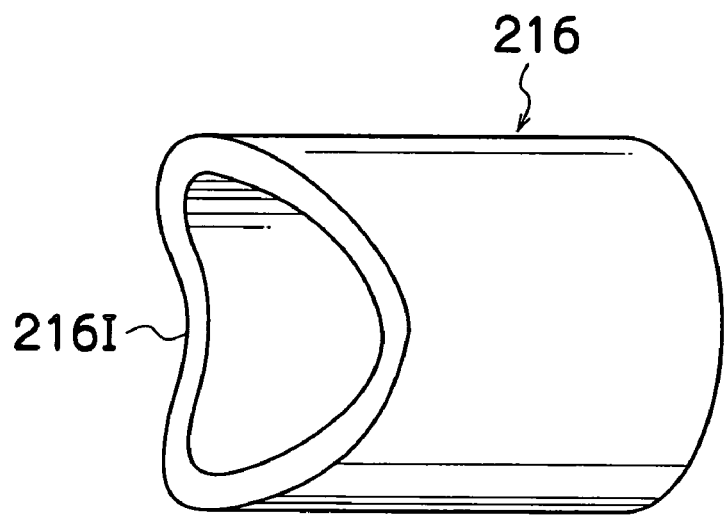
FIG. 14 is a perspective diagram to show a hood member having a different configuration from that of FIG. 2.
Figure 15:
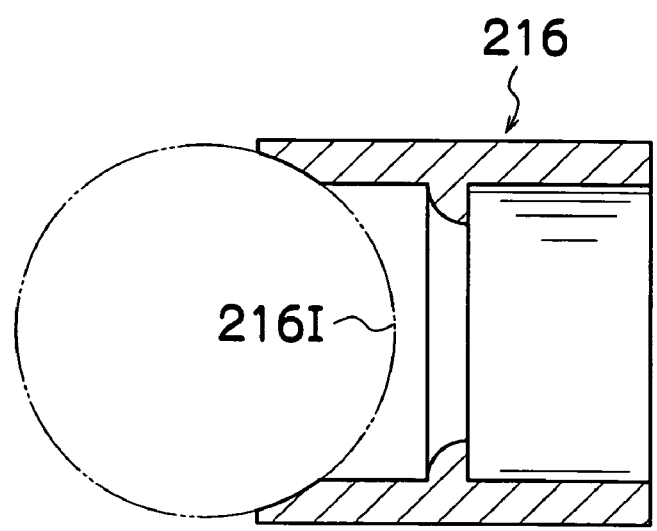
FIG. 15 is a side view of the hood member of FIG. 14.

A hood member 216 shown in FIGS. 14 and 15 includes a distal end portion 216A which is provided with a circular groove 216I. The side of a medical capsule 220 is pulled into the groove 216I to be held, so that the medical capsule 220 can be reliably held.

The above embodiment has been explained by an example in which a medical capsule 220 in a body cavity is held to be collected at outside of the body cavity, but the embodiment may be used in an application to transport a held medical capsule 220 through a body cavity. For example, when a medical capsule 220 is stuck at a narrowed portion of a body cavity, the held medical capsule 220 is transported beyond the narrowed portion, and is released. A release of a medical capsule 220 is performed by controlling the suction button 30 of FIG. 1 to stop a sucking operation through the forceps port 58.

The embodiment may be also used in an application to transport a medical capsule 220 into a body cavity by inserting the inserting section 12 into the body cavity after a medical capsule 220 is held by the inserting section 12 at the outside of the body cavity.

The above embodiment has been explained as an example in which the present invention is applied to a double balloon endoscopic apparatus having a first balloon 60 and a second balloon 80, but a configuration of an endoscopic apparatus according to the present invention is not limited to this, and the present invention may be applied to an endoscopic apparatus without a first balloon 60 and a second balloon 80, or an endoscopic apparatus without an insertion assisting tool 70. That is, a hood member 200 is attached to a distal end portion 44 of an inserting section 12 of an endoscope 10, and the inside of the hood member 200 is made vacuum through a forceps port 58 to attract a medical capsule 220 to the distal end of the hood member 200 so that the medical capsule 220 can be reliably held for its collection or transportation.

What is claimed is:

1. A method for collecting/transporting a medical capsule by holding the medical capsule using an endoscopic apparatus which has an endoscope having an inserting section to be inserted in a body cavity with a distal end including an observation section to observe a subject and a suction opening, a sucking device in communication with the suction opening, and a generally cylindrical hood member which is attached to the distal end of the inserting section, wherein
the hood member is a generally cylindrical member having:
at least two internal areas of a base end side internal space area and a distal side internal space area in a direction of an insertion shaft of an inserting section, and
a distal end with an outer circumferential surface of the hood member is formed with a plurality of grooves which extend along a longitudinal direction of the hood member, and each of the grooves is provided at intervals along a circumferential direction of the hood member, the method comprising:
an attaching step of fitting and attaching the distal end of the inserting section to the base end side internal space area in a direction from the base end towards the distal end along the insertion shaft,
a sucking step of storing the medical capsule into the distal side internal space area in a direction from the distal end towards the base end along the insertion shaft and actuating to suck the inside of the distal side internal space area that stored the medical capsule via the suction opening to make in said inside a low pressure vacuum; and
a holding step of attracting and holding the medical capsule to the hood member sucked by the sucking step,
wherein said grooves allow the distal end of the hood member to be deflected for holding the medical capsule.

2. An endoscopic apparatus, comprising:
an endoscope having an inserting section to be inserted in body cavity with a distal end including an observation section to observe a subject and a suction opening;
a sucking device in communication with the suction opening; and
a generally cylindrical hood member which is attached to the distal end of the inserting section, wherein
the hood member is a generally cylindrical member having
at least two internal areas of a base end side internal space area and a distal side internal space area in a direction of an insertion shaft of the inserting section, and
a distal end with an outer circumferential surface of the hood member is formed with a plurality of grooves which extend along a longitudinal direction of the hood member, and each of the grooves is provided at intervals along a circumferential direction of the hood member, the base end side internal space area is an attaching section to fit and attach the distal end of the insertion section in a direction from the base end to the distal end along an insertion shaft, and
the distal side internal space area is a holding section to attract and hold a medical capsule when storing the medical capsule in a direction from the distal end towards the base end along the insertion shaft,
wherein said grooves allow the distal end of the hood member to be deflected for holding the medical capsule, and
wherein the sucking device is actuated to suck the inside of the distal side internal space area that stored the medical capsule via the suction opening to make said inside a low pressure vacuum.

3. The endoscopic apparatus according to claim 2, wherein the hood member is configured to hold a medical capsule with at least a part of the medical capsule being pulled into the inside of the hood member.

4. The endoscopic apparatus according to claim 2, wherein at least a part of the hood member is transparent or semi-transparent.

5. The endoscopic apparatus according to claim 3, wherein at least a part of the hood member is transparent or semi-transparent.

6. The endoscopic apparatus according to claim 2, further comprising:
a first expandable and contractible balloon which is mounted to an outer circumferential surface of a distal end of the inserting section;
an insertion assisting tool into which the inserting section is inserted to be guided in a body cavity; and
a second expandable and contractible balloon which is mounted to an outer circumferential surface of the insertion assisting tool.

7. The endoscopic apparatus according to claim 3, further comprising:
a first expandable and contractible balloon which is mounted to an outer circumferential surface of a distal end of the inserting section;
an insertion assisting tool into which the inserting section is inserted to be guided in a body cavity; and
a second expandable and contractible balloon which is mounted to an outer circumferential surface of the insertion assisting tool.

8. The endoscopic apparatus according to claim 4, further comprising:
a first expandable and contractible balloon which is mounted to an outer circumferential surface of a distal end of the inserting section;
an insertion assisting tool into which the inserting section is inserted to be guided in a body cavity; and
a second expandable and contractible balloon which is mounted to an outer circumferential surface of the insertion assisting tool.

9. The endoscopic apparatus according to claim 5, further comprising:

a first expandable and contractible balloon which is mounted to an outer circumferential surface of a distal end of the inserting section;

an insertion assisting tool into which the inserting section is inserted to be guided in a body cavity; and a second expandable and contractible balloon which is mounted to an outer circumferential surface of the insertion assisting tool.

10. The endoscopic apparatus according to claim 2, wherein the holding section includes a distal end of the hood member having an inner circumferential surface which has a curved portion corresponding to a curved shape of the medical capsule.

11. The endoscopic apparatus according to claim 2, wherein the holding section is configured to include a distal end of the hood member which is formed thinner than any other parts of the hood member.

12. The endoscopic apparatus according to claim 2, wherein the holding section is configured to include a distal end of the hood member having an inner circumferential surface in which a groove is formed in the circumferential direction.

13. The endoscopic apparatus according to claim 1, wherein a plurality of the grooves are provided in a direction along a central axis of the hood member with ribs being formed between the grooves.

* * * * *